(12) United States Patent
Revol-Cavalier et al.

(10) Patent No.: US 9,955,908 B2
(45) Date of Patent: May 1, 2018

(54) DEVICE AND METHOD FOR DETERMINING AN EXCRETION FLOW RATE OF A BODY FLUID OF A PERSON OR AN ANIMAL

(75) Inventors: Frédéric Revol-Cavalier, Seyssins (FR); Aurélien Lambert, Saint Jean de Sixt (FR)

(73) Assignee: COMMISSARIAT À L'ENERGIE ATOMIQUE ET AUX ENERGIES ALTERNATIVES, Paris (FR)

(*) Notice: Subject to any disclaimer, the term of this patent is extended or adjusted under 35 U.S.C. 154(b) by 1627 days.

(21) Appl. No.: 13/325,441

(22) Filed: Dec. 14, 2011

(65) Prior Publication Data

US 2012/0150072 A1    Jun. 14, 2012

(30) Foreign Application Priority Data

Dec. 14, 2010  (FR) ...................................... 10 04864

(51) Int. Cl.
| A61B 5/00 | (2006.01) |
| A61B 5/145 | (2006.01) |
| G01N 33/487 | (2006.01) |
| A61B 5/20 | (2006.01) |
| A61F 13/42 | (2006.01) |

(52) U.S. Cl.
CPC ........ *A61B 5/4266* (2013.01); *A61B 5/14517* (2013.01); *G01N 33/48707* (2013.01); *A61B 5/20* (2013.01); *A61F 13/42* (2013.01)

(58) Field of Classification Search
CPC ............... A61B 5/14517; A61B 5/4266; A61F 13/42–13/44
See application file for complete search history.

(56) References Cited

U.S. PATENT DOCUMENTS

| 5,050,604 A | 9/1991 | Reshef et al. | |
| 5,882,931 A | 3/1999 | Petersen | |
| 7,141,715 B2* | 11/2006 | Shapira .................... | A61F 13/42 340/573.6 |
| 7,834,234 B2* | 11/2010 | Roe .......................... | A61F 13/42 604/361 |
| 7,855,653 B2* | 12/2010 | Rondoni ................. | A61F 13/42 340/539.12 |

(Continued)

FOREIGN PATENT DOCUMENTS

| FR | 2 669 529 A1 | 5/1992 |
| JP | A-09-051877 | 2/1997 |

(Continued)

*Primary Examiner* — Rene Towa
*Assistant Examiner* — H. Q. Nguyen
(74) *Attorney, Agent, or Firm* — Oliff PLC (57) ABSTRACT

A device and method for determining an excretion flow rate of a body fluid of a person or an animal. The device includes an absorbent element equipped with at least three electrodes connected to a measuring system for measuring at least one electric parameter so as to be electrically coupled two by two and to form at least two pairs of electrodes, separating systems which include an inlet opening exposing a part of the absorbent element so as to create a diffusion path. At least two of the electrodes are first electrodes placed along the diffusion path in such a way that each of the first electrodes is at a distance from the inlet opening representative of a volume of absorbed fluid.

20 Claims, 9 Drawing Sheets

(56) References Cited

U.S. PATENT DOCUMENTS

| | | | |
|---|---|---|---|
| 2010/0063372 A1* | 3/2010 | Potts | A61B 5/14521 600/346 |
| 2010/0200400 A1* | 8/2010 | Revol-Cavalier | A61B 5/14507 204/416 |
| 2011/0079521 A1* | 4/2011 | Revol-Cavalier | A61B 5/4266 205/789 |
| 2011/0312740 A1* | 12/2011 | Silverbrook | B01L 3/5027 506/39 |

FOREIGN PATENT DOCUMENTS

| | | |
|---|---|---|
| JP | A-2010-046196 | 3/2010 |
| WO | WO 02/091917 A1 | 11/2002 |

\* cited by examiner

DEVICE AND METHOD FOR DETERMINING AN EXCRETION FLOW RATE OF A BODY FLUID OF A PERSON OR AN ANIMAL

BACKGROUND OF THE INVENTION

The invention relates to a device for determining an excretion flow rate of a body fluid of a person or an animal comprising:
- an absorbent element absorbing body fluid equipped with at least one pair of electrodes $C_i$ electrically connected to means for measuring at least one electric parameter $X_i$ of the part of said element situated between said pair of electrodes $C_i$ and,
- separating means supporting said absorbent element, designed to be placed in contact with a source of excretion of the body fluid and arranged between said source and said absorbent element, said separating means comprising an opening for inlet of the body fluid exposing a part of the absorbent element so as to create a diffusion path of the body fluid through said absorbent element.

The invention also relates to a method for determining an excretion flow rate of a body fluid of a person or an animal.

STATE OF THE ART

Numerous works have highlighted the advantages of a good hydration for persons in particular when indulging in physical sports activities or for fragile individuals such as infants or elderly people. Hydric losses due to perspiration or lack of hydration can lead to the appearance of physiological disorders such as loss of weight, extreme fatigue or dizziness. For the most severe cases of dehydration, loss of intellectual faculties or physiological disorders able to lead to death of the person or of the animal can also occur.

To prevent dehydration or overhydration, one approach consists in evaluating the hydric loss by sweating i.e. the quantity of sweat perspired over a given time. This evaluation is conventionally performed by weighing on differential scales. The person is weighed several times throughout a physical exercise or in the course of a medical check-up to be able to calculate the ratio between the hydric loss and the weight of the person. This ratio is characteristic of the degree of dehydration of the person and consequently of his/her state of hydration. This solution is precise and sensitive, but nevertheless only remains applicable in a laboratory and is not able to be suitable for mobile applications.

Recent works have proposed devices enabling the hydric loss of a person to be evaluated from measurement of the level of perspiration secreted during a physical exercise or a heart attack.

Figure 1:
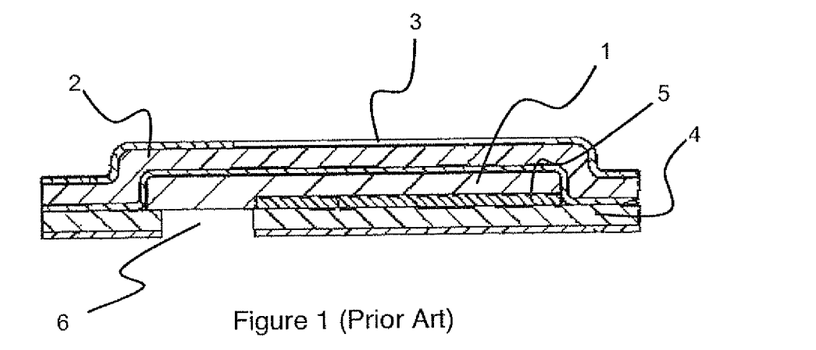
FIG. 1 schematically represents a sweat measuring device according to the prior art, in cross-section.

For example purposes represented in FIG. 1, the document JP-A-2010046196 describes a sweat measuring device comprising a sweat-absorbing material 1 arranged between a first film 2 having a transparent window 3 and a second film 4. The absorbent material 1 is provided with a colored indicator 5 that changes color in contact with the sweat. Colored indicator 5 is associated with a graduated scale enabling a correspondence to be made between the coloration of absorbent material 1 and a quantity of sweat secreted by the human body. An opening 6 is made in second film 4 to expose absorbent material 1 and to enable inlet of sweat to absorbent material 1 and absorption by the latter. The sweat measuring device simply enables the quantity of secreted sweat to be measured by visualizing the progression of the sweat stained by colored indicator 5 along absorbent material 1. Nevertheless, the use of such a sweat measuring device is limited to applications where it is possible to position the device on visible parts of the human body. Only a single reading is able to be made on completion of the physical exercise or at the outcome of the heart attack when the measuring device can only be applied on non-visible parts.

Numerous applications do however require sweat monitoring in real time and do not enable the measuring device to be applied only on visible parts of a person's body. Such a measuring device is for example unsuitable for monitoring an intense physical activity where the hydric loss is great and/or an activity performed under particular working conditions such as in civil or military security where it is compulsory to wear airtight protective clothing, which is often opaque, protecting against radioactivity, chemical or biological risks.

The efficiency of a sweat measuring device further depends in particular on its positioning on the human body as sweat is secreted in heterogeneous manner depending on the part of the human body considered. Perspiration is in fact concentrated in certain areas such as the back and the thorax, which are usually concealed by an item of clothing.

Figure 2:
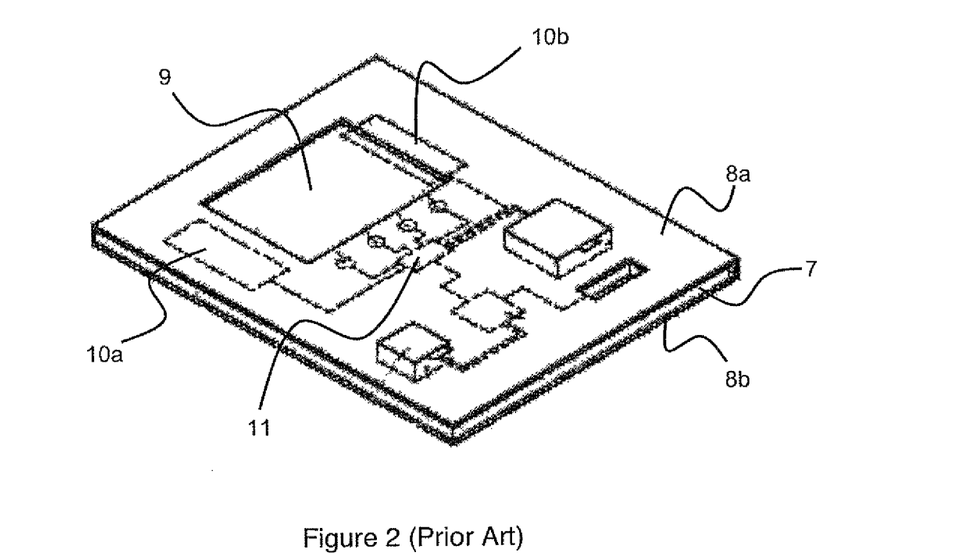
FIG. 2 schematically represents another sweat measuring device according to the prior art, in perspective view.

The document JP-A-9051877 proposes a flexible device applied on a person's body and which enables an emitted quantity of sweat to be measured and recorded in real time. As represented in FIG. 2, the flexible device comprises a body 7 that is permeable to sweat, arranged between two impermeable plastic films 8a and 8b. One of the films 8a is provided with an opening 9 and comprises an adhesive surface for fixing the device onto a person's skin. Two identical electrodes, 10a and 10b, are arranged in body 7 of the device and connected to a measuring circuit 11 to enable conductivity values between the two electrodes 10a and 10b to be measured. Measurement is based on the principle that a variation of conductivity of the medium comprised between the two electrodes, 10a and 10b, is representative of the secretion rate by the person and enables measurement of the secretion rate to be established. Such an interpretation does not however take account of other parameters which may also affect the precision of measurement. The conductivity value does in fact also depend on the ionic concentration of the sweat. The ionic concentration of the sweat can however vary independently from the quantity of sweat secreted, for example according to the intensity of the physical activity or in the course of the day. Likewise, evaporation of the sweat at the periphery of the device can also create a concentration gradient within body 7 and make interpretation of the results difficult, rendering the measurements erroneous. Finally, the use of the two same electrodes 10a and 10b for the successive measurements can impair the precision of the device in the course of time.

OBJECT OF THE INVENTION

The object of the invention is to provide a device that is precise and dependable, enabling an excretion flow rate of a body fluid of a person or an animal to be evaluated quickly, in real time and continuously.

It is a further object of the invention to propose an embedded device that is easy to use, for a wide field of application.

In particular, it is a further object of the invention to propose a device for determining a sweat excretion flow rate enabling the hydric loss by sweating of the person or of an animal to be evaluated.

According to the invention, this object is achieved by the appended claims and more particularly by the fact that the absorbent element comprises at least three electrodes spaced apart from one another and connected to the measuring means so as to be electrically coupled two by two and to form at least two pairs of electrodes $C_i$ and by the fact that at least two of the electrodes are first electrodes $E^1_i$ placed in sequential manner along the diffusion path so that each of said first electrodes $E^1_i$ is at a distance $d_i$ from the inlet opening representative of a volume $V_i$ of body fluid absorbed by the absorbent element.

It is a further object of the invention to provide a method that is simple to implement and uses such a device enabling an excretion level $Q_i$ of a body fluid of a person or an animal to be determined in precise and reproducible manner to obtain a global excretion flow rate and/or an instantaneous excretion flow rate from said excretion level $Q_i$.

BRIEF DESCRIPTION OF THE DRAWINGS

Other advantages and features will become more clearly apparent from the following description of particular embodiments of the invention, given for non-restrictive example purposes only and represented in the appended drawings in which.

DESCRIPTION OF PARTICULAR EMBODIMENTS

The object of the invention is to provide a device enabling the excretion level $Q_i$ or the excretion flow rate of a body fluid of a person or an animal to be determined. The device is advantageously designed for embedded use on any person or animal able to excrete a body fluid. Use of the device is preferably performed continuously and in real time, for direct reading of the excretion level of a body fluid. In the present description, the excretion level will in fact advantageously serve the purpose of determining an excretion flow rate of a body fluid, which may for example be of global or instantaneous type. Thus, in the following, when the term level is referred to, the notion of level can be replaced by the notion of flow rate.

The body fluid can for example be sweat or urine. The device can be integrated in an item of clothing for determining the perspiration flow rate or in diapers for determining the urine excretion level or the urine excretion flow rate.

Figure 3:
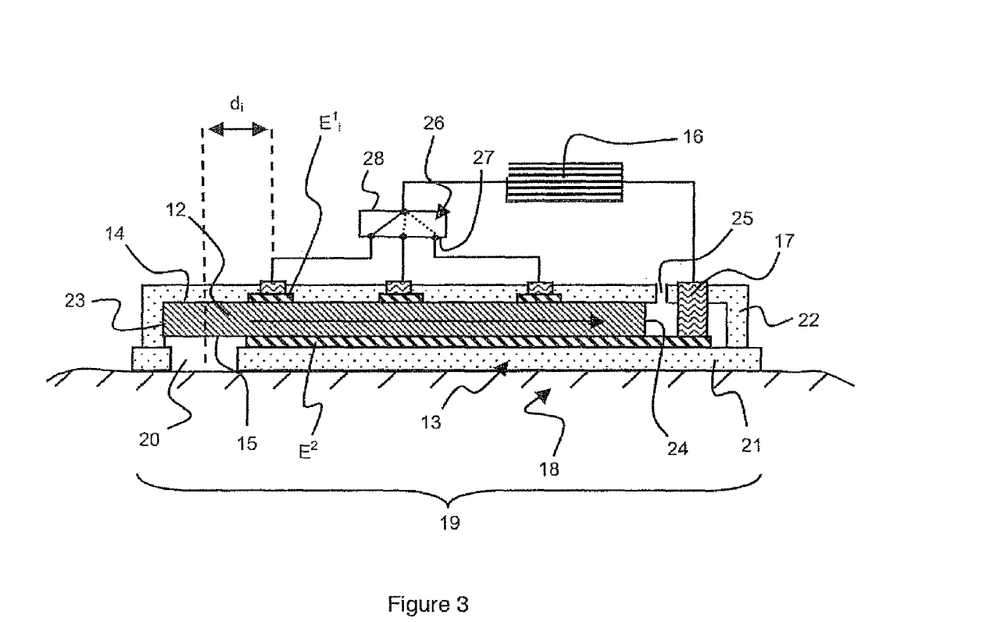
FIGS. 3 and 4 schematically represent a device for determining an excretion flow rate of a body fluid according to a particular embodiment of the invention, respectively in cross-section and in top view.
Figure 4:
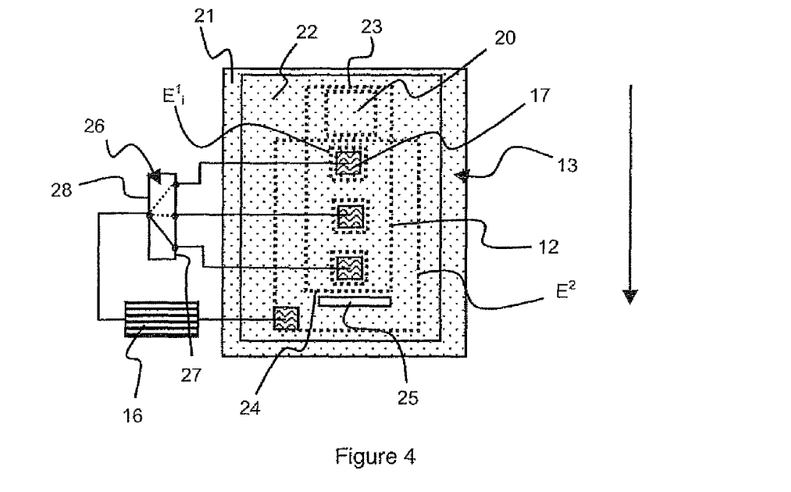

According to a first particular embodiment represented in FIGS. 3 and 4, the device for determining an excretion level $Q_i$ or an excretion flow rate of a body fluid of a person or an animal comprises an absorbent element 12 absorbing the body fluid and separating means 13 supporting absorbent element 12. Separating means 13 are preferably impermeable. When absorbent element 12 is arranged along the body of the person or of the animal, impermeable separating means 13 support the absorbent element 12 and perform isolation with respect to the body of the person.

Absorbent element 12 can have a main first surface 14 and a second main surface 15 opposite said main first surface 14. Absorbent element 12 can advantageously be chosen from absorbent paper, a fabric and a part of an item of clothing.

Absorbent element 12 also comprises at least three electrodes spaced apart from one another and advantageously formed from the same material.

The electrodes are electrically connected to measuring means also called measuring systems 16 for measuring at least one electric parameter $X_i$ so as to be electrically coupled two by two to form at least two pairs of electrodes $C_i$. Contact connections 17 are provided on each electrode to perform electric connection of the latter to electric measuring means 16.

Separating means also called separating systems 13, which are preferably impermeable, are designed to be placed in contact with a source of excretion of the body fluid and arranged between the source of the excretion of the body fluid and the absorbent element 12. The source of excretion of the body fluid is for example the skin 18 of a person or of an animal. Separating means 13 can be formed by a material that is impermeable to the body fluid i.e. which prevents the body fluid from passing through impermeable separating means 13. Separating means 13 are for example made from a plastic material chosen from polyethylene, polystyrene, polyacrylic, polyethane, polyimide, polyimide, polyester, silicone, polytetrafluoroethylene (PTFE) and hollow fibres, impermeable to liquids and letting water vapor pass.

As represented in FIG. 3, separating means 13 have in particular an external part 19 designed to be applied on skin 18, which can advantageously be coated by an adhesive material such as glue to fix the device to the person or to the animal and to keep it in place throughout the duration of the measurements for determining excretion level $Q_i$. The device can thus be used as an embedded device.

Impermeable separating means 13 comprise an inlet opening 20 of the body fluid exposing a part of second main surface 15 of absorbent element 12 so as to create a diffusion path of the body fluid through absorbent element 12.

What is meant by diffusion path is the path taken by a diffusion front of a liquid which moves in an absorbent element 12 starting from the inlet opening 20, and which moves away from this inlet opening 20.

The body fluid diffusion path is preferably unidirectional. What is meant by unidirectional is the fact that the body fluid migrates from the inlet opening 20 to a same area, in a single specific direction represented by the arrow in FIGS. 3 and 4.

Inlet opening 20 is preferably located at the level of external part 19 of separating means 13.

Impermeable separating means 13 enable absorbent element 12 to be isolated from skin 18 and to ensure passage of the body fluid excreted by skin 18 through inlet opening 20.

Impermeable separating means 13 are advantageously formed by an impermeable enclosure in which absorbent element 12 is housed.

As illustrated in the example of FIGS. 3 and 4 and in a manner that is subsequently applicable to the different embodiments, the electrodes associated with absorbent element 12 are not located facing inlet opening 20. In other words, the electrodes are located at a distance from inlet opening 20.

As represented in FIG. 3, impermeable enclosure can for example be formed by first and second impermeable films, respectively 21 and 22, hermetically joined to one another so as to form the housing of absorbent element 12. Contact connections 17 pass through the enclosure to perform electric connection of the electrodes with electric measuring means 16.

External part 19 of impermeable separating means 13 is preferably located at the level of first impermeable film 21. External part 19 can for example constitute the external surface of first impermeable film 21.

Inlet opening 20 is arranged in first impermeable film 21 so as to pass through the whole thickness of first impermeable film 21.

As represented in FIGS. 3 and 4, second impermeable film 22 preferably completely covers absorbent element 12, in particular first main surface 14, to isolate absorbent element 12 from the outside environment and in particular to protect it against surrounding moisture. The impermeable enclosure thereby guarantees the exactness of the measurements and prevents any errors due to variations of the hygrometry or temperature of the environment.

Absorbent element 12 is for example in the form of a strip having a length advantageously comprised between 10 mm and a few hundred millimeters, preferably between 10 mm and 100 mm, and a width advantageously comprised between a few millimeters and a few tens of millimeters, preferably between 2 mm and 10 mm. The strip has first and second ends, respectively 23 and 24, corresponding to the width of the strip. Inlet opening 20 is situated in proximity to first end 23, for example at a distance from first end 23 of less than 5% of the length of the strip. The diffusion path thereby begins at inlet opening 20 and continues along the strip to second end 24 (arrow in FIGS. 3 and 4).

The enclosure advantageously comprises an outlet opening 25 of the body fluid located at the level of second end 24 of absorbent element 12 to enable removal of the body fluid that has migrated all along the diffusion path up to second end 24. Outlet opening 25 can be made through second impermeable film 22.

At least two of the electrodes are first electrodes $E^1_i$ arranged at the level of first main surface 14 of absorbent element 12 and placed in sequential manner along the diffusion path so that each of first electrodes $E^1_i$ is at a distance $d_i$ from inlet opening 20.

As represented in FIG. 3, first electrodes $E^1_i$ are arranged on first main surface 14 of absorbent element 12.

i represents the rank of electrode $E^1_i$ in the formed sequence. Rank i increases when going from a first electrode $E^1_i$ to another adjacent first electrode $E^1_{i+1}$, when moving away from inlet opening 20.

For a better understanding of the invention and for the sake of clarity, when the description applies indifferently to any one of first electrodes $E^1_i$ or to one of its characteristics, the index i will be used in the remainder of the description to identify the electrode or one of its characteristics. When the description applies to a first electrode in particular or to a specific characteristic of said first electrode, the corresponding rank of the first electrode considered will on the other hand be used instead of index i. $E^1_i$ will thus be used to identify any one of the first electrodes $E^1_1$, $E^1_2$ or $E^1_3$, and $E^1_1$ will be used if it is desired to identify only the first electrode $E^1$ of rank i=1.

For each first electrode $E^1_i$, distance $d_i$ complies with the following two conditions (1) and (2):

$$d^1_i > 0 \text{ and} \tag{1}$$

$$d^1_i < d^1_{(i+1)} \tag{2}$$

Each distance $d_i$ is representative of the volume $V_i$ of body fluid absorbed by absorbent element 12. A position of first electrode $E^1_i$ on the diffusion path is consequently representative of the volume $V_i$ of body fluid absorbed by absorbent element 12. Volume $V_i$ can advantageously be a mean volume calculated from a range of volumes.

Correlation between volumes $V_i$ and distances $d_i$ is performed conventionally by calibration, prior to determination of excretion level a of the person or animal. What is meant by excretion level $Q_i$ is the quantity of body fluid excreted by the person or animal.

A look-up table further enables each volume $V_i$ to be linked to a given excretion level $Q_i$. Excretion level $Q_i$ a can be obtained by extrapolation, according to any known method, possibly taking account of several characteristic parameters of the person or the animal, in particular the area of skin 18 on which device is applied, the sex, weight, height and age of the person or of the animal.

As represented in FIG. 3, the device preferably comprises at least three first electrodes $E^1_i$. First electrodes $E^1_i$ are preferably arranged in line in the direction of the diffusion path (arrow in FIGS. 3 and 4). First electrodes $E^1_i$ are arranged between the enclosure and first main surface 14 of absorbent element 12. Second impermeable film 22 covers first electrodes $E^1_i$ arranged on first main surface 14 of absorbent element 12.

At least one of the electrodes is advantageously a second electrode $E^2$ arranged between impermeable separating means 13 and second main surface 15 of absorbent element 12.

Second electrode $E^2$ is in direct contact with second main surface 15 of absorbent element 12 so that the diffusion path of the body fluid passes between second electrode $E^2$ and first electrodes $E^1_i$.

Alternatively, instead of being on absorbent element 12, first electrodes $E^1_i$ and/or second electrode $E^2$ can be arranged in absorbent element 12 provided that at least a part of absorbent element 12 separates first electrodes $E^1_i$ from second electrode $E^2$. First electrodes $E^1_i$ are then located at the level of first main surface 14 and/or second electrode $E^2$ is located at the level of second main surface 15.

First electrodes $E^1_i$ and second electrode $E^2$ are preferably made from metal. First electrodes $E^1_i$ and second electrode $E^2$ are for example made from copper, aluminum, gold, platinum, carbon or indium oxide. First electrodes $E^1_i$ and second electrode $E^2$ can also comprise a conducting polymer or a polymer conventionally rendered conductive by addition of metal particles such as silver or gold or carbon particles.

Absorbent element 12 is provided with at least two pairs of electrodes $C_i$ connected to the measuring means 16. The device advantageously comprises a single second electrode $E^2$ able to be electrically coupled with each of first electrodes $E^1_i$, which forms as many pairs of electrodes $C_i$.

An electric selector switch 26 with several channels connects first electrodes $E^1_i$ to electric measuring means 16 and enables each first electrode $E^1_i$ to be selectively coupled with second electrode $E^2$ to form pairs of electrodes $C_i$.

As represented in FIGS. 3 and 4, electric selector switch 26 presents first and second terminals, respectively 27 and 28, enabling three possible positions of electric selector switch 26, positions 1, 2 and 3. First electrodes $E^1_1$, $E^1_2$ and $E^1_3$ are connected to first terminal 27 of electric selector switch 26. By choosing the position of electric selector switch 26, second electrode $E_2$ can be electrically coupled with at least one of first electrodes $E^1_i$. Likewise, each first electrode $E^1_i$ can be successively coupled with second electrode $E^2$ and form a pair of electrodes $C_i$, by successive switching from one position to another. Switching to positions 1, 2 and 3 respectively enables the pairs of electrodes $C_1$, $C_2$ and $C_3$ to be formed by connecting corresponding first electrodes $E^1_1$, $E^1_2$ and $E^1_3$ to electric measuring means 16.

Electric measuring means 16 are connected to second electrode $E^2$ and a second terminal 28. Electric measuring means 16 are designed to measure an electric resistance, a conductivity, an electric voltage, or to make an electrochemical measurement or a capacitance measurement, for each pair of electrodes $C_i$ formed.

The specific shape of absorbent element 12 and the position of inlet opening 20 relatively to the position of absorbent element 12 define the diffusion path. The body fluid absorbed creates a diffusion front 29 on the diffusion path passing consecutively between each pair $C_i$ of electrically paired electrodes.

Flow of the body fluid in the absorbent element 12 modifies the electric characteristics $X_i$ of the part of absorbent element 12 located between the electrodes of a pair $C_i$. The characteristics are for example the conductivity, the resistance or the capacitance. Monitoring of electric parameters $X_i$, for the different electrode pairs $C_i$, thereby enables the position of diffusion front 29 of the body fluid in absorbent element 12 to be determined. The position of diffusion front 29 can further be correlated with body fluid excretion level $Q_i$, and advantageously the instantaneous excretion flow rate $D_i$ and global excretion flow rate $D_g$.

Likewise, according to a known principle, application of a voltage between first electrode $E^1_i$ and second electrode $E^2$ of a pair $C_i$ induces a hydrolysis current of the body fluid present in absorbent element 12 in the imbibed state, which is able to be detected and monitored by electrochemical measurements.

The device further conventionally comprises a data control and operating system (not shown) enabling the data from electric measuring means 16 to be collected and processed, and the position and speed of switching of electric selector switch 26 to be managed if required. The data control and operating system can be a computer, a remote-located control device, or a portable computer of PDA (Personal Digital Assistant) type. The data control and operating system can enable an alarm to be triggered if required.

The data control and operating system can be integrated in the device in the form of a printed circuit board or an ASIC (Application Specific Integrated Component).

Alternatively, the device can comprise hardwired or wireless data transmission means (not shown) to enable transfer of the data to the data control and operating system.

Figure 5:
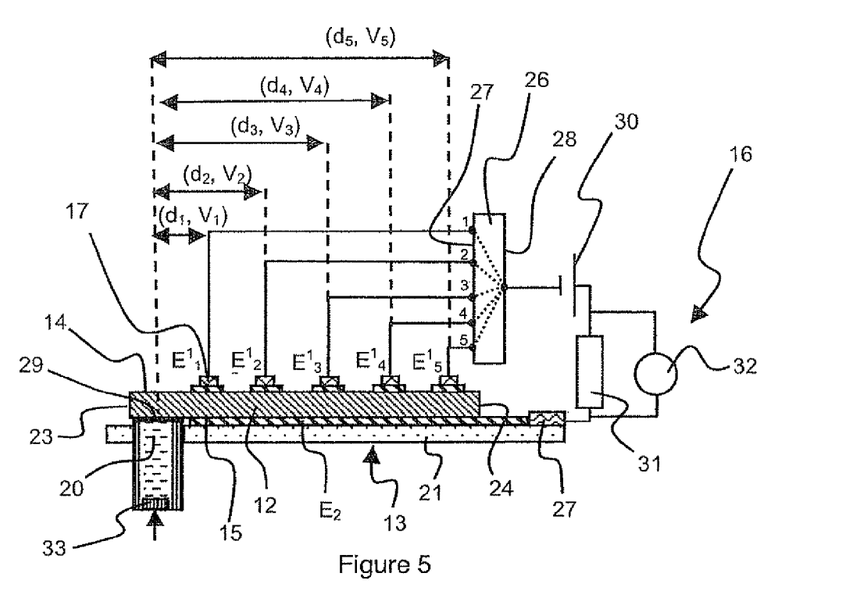
FIGS. 5 to 10 schematically represent different steps of a method for determining an excretion flow rate of a body fluid from an excretion level of the body fluid according to the invention, in cross-section.
Figure 6:
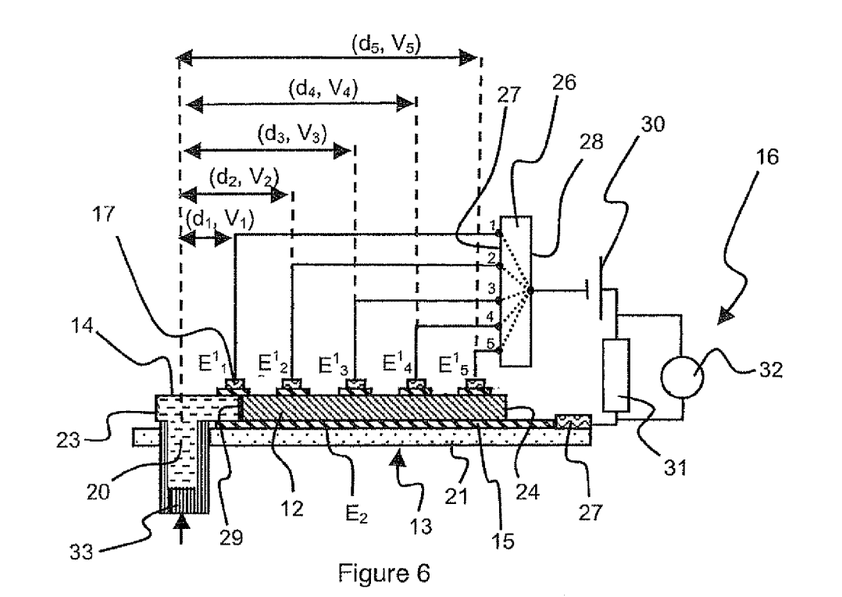
Figure 7:
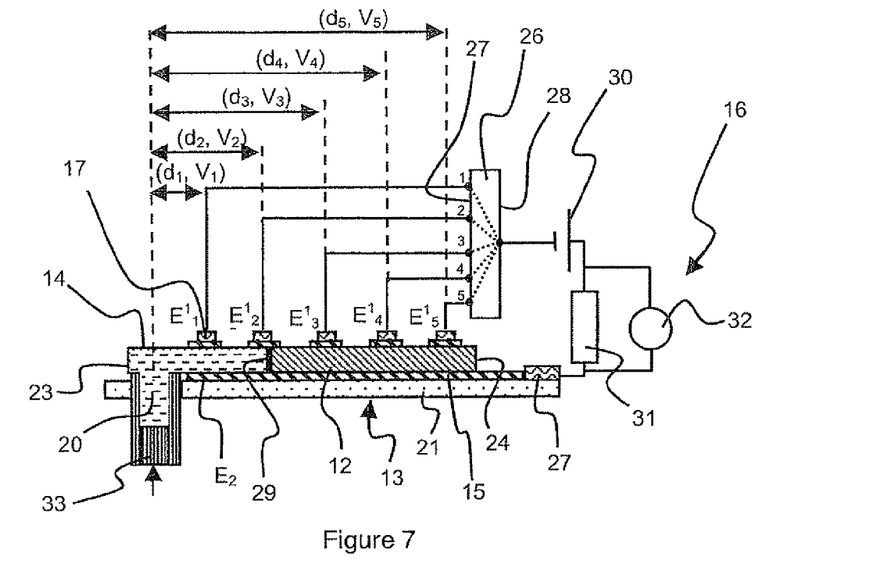
Figure 8:
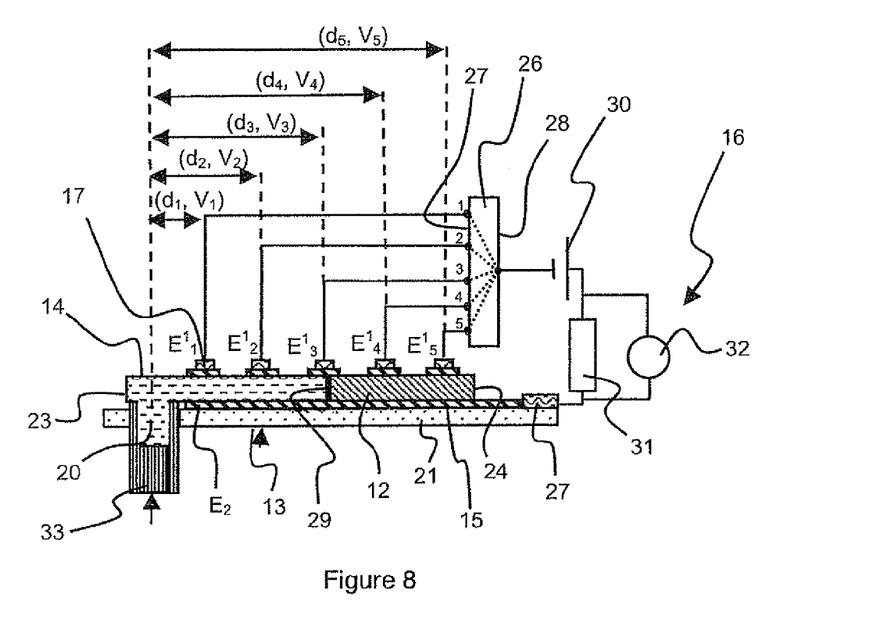
Figure 9:
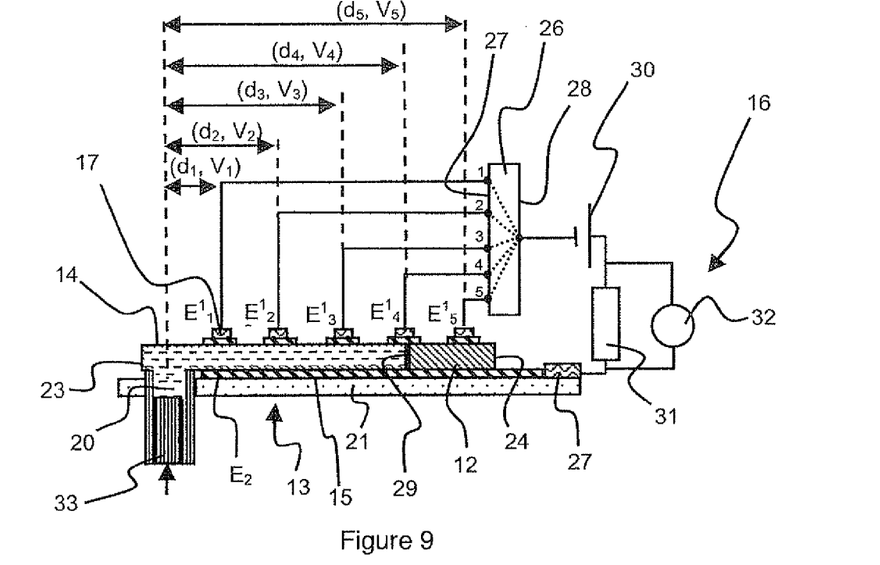
Figure 10:
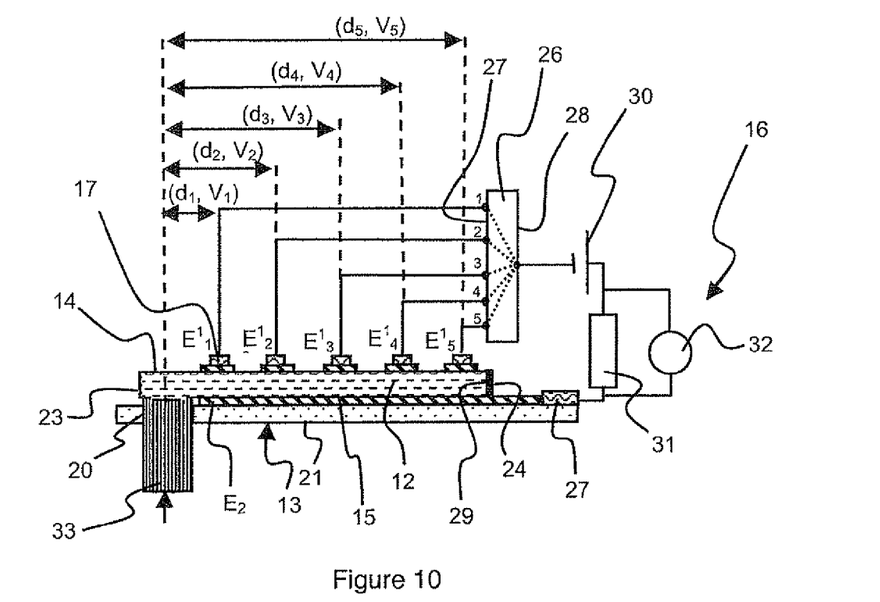

According to a second particular embodiment represented in FIG. 5, a device for determining excretion level $Q_i$ (or excretion flow rate) differs from the first embodiment described in the foregoing in that it comprises five first electrodes $E^1_1$, $E^1_2$, $E^1_3$, $E^1_4$ and $E^1_5$ respectively forming five pairs of electrodes $C_1$, $C_2$, $C_3$, $C_4$ and $C_5$ by electric coupling with second electrode $E^2$. Electric selector switch 26 thus comprises a first terminal 27 with five channels connected to first electrodes $E^1_1$, $E^1_2$, $E^1_3$, $E^1_4$ and $E^1_5$ and a second terminal 28 connected to electric measuring means 16.

The device further differs from the device described in the foregoing in that impermeable separating means 13 are only formed by first impermeable film 21.

Electric measuring means 16 are constituted by an electric generator 30 in series with a resistor 31. A voltmeter 32 is connected in parallel to the terminals of resistor 31 to measure the voltage at the terminals of this resistor 31. Electric coupling of each pair of electrodes $C_i$, $C_2$, $C_3$, $C_4$ or $C_5$ is performed by respectively switching to position 1, 2, 3, 4 or 5.

According to a particular embodiment, a method for determining an excretion level/flow rate of a body fluid of a person or an animal using a device according to the second embodiment described above comprises a first step of placing the device in contact with a source of excretion of the body fluid. The source of excretion of the body fluid is advantageously a localized area of skin 18 of the person or animal.

The device can for example be applied on the localized area of skin 18 so as to place impermeable separating means 13 in contact with skin 18 and to position inlet opening 20 facing skin 18. External part 19 of first impermeable film 21 adheres to skin 18 over the whole localized area.

Contacting is performed in such a way as to ensure that the excreted body fluid passes through inlet opening 20 to absorbent element 12. The body fluid excreted by skin 18 is consequently channel to absorbent element 12.

The body fluid inlet in this way into the device via inlet opening 20 is then in contact with absorbent element 12 and impregnates absorbent element 12. The body fluid migrates within absorbent element 12 along the diffusion path, in the unidirectional direction of diffusion (arrow in FIG. 5).

After application of the device, an electric parameter $X_i$ is measured for each pair of electrodes $C_i$.

The electric parameter $X_i$ measured is chosen from a conductivity, a voltage, a resistance, a capacitance and/or a global ion concentration.

The series of measurements is performed successively from one pair of electrodes $C_i$ to the adjacent pair of electrodes $C_{(i+1)}$ in the sequential order imposed by the diffusion path.

As represented in FIG. 5, X1, X2, X3, X4 and X5 respectively corresponding to each pair C1, C2, C3, C4 and C5 are successively measured. The series of measurements can, if required, be repeated as many times as necessary, in the same sequential order, in order to perform scanning on the five pairs of electrodes Ci.

The series of measurements of electric parameter $X_i$ can be performed by successive switching of electric selector switch 26 from position 1 to position 5 with a set switching speed.

Positioning of diffusion front 29 depends on volume $V_i$ of body fluid inlet via inlet opening 20. When diffusion front 29 passes a first electrode $E^1_i$, the part of absorbent element 12 situated under first electrode $E^1_i$ goes from a dry state to an impregnated state which results in a modification of the conductive properties of this part. The value of electric parameter $X_i$ varies until a threshold value $X_{is}$ is reached.

Threshold value $X_{is}$ is a predefined value corresponding to the flow of the body fluid between the electrodes of pair of electrodes $C_i$. Threshold value $X_{is}$ corresponds to the value of the electric parameter $X_i$ obtained when the part of absorbent element 12 situated between the electrodes of pair $C_i$ is imbibed with body fluid. Threshold value $X_{is}$ is typically obtained by prior calibration by means of any known method for each pair of electrodes $C_i$.

The position of a diffusion front 29 of the body fluid on the diffusion path is therefore evaluated relatively to the position of first electrodes $E^1_i$ by comparison of the value of the measured electric parameter $X_i$ with threshold value $X_{is}$.

Knowing that the position of each first electrode $E^1_i$ is associated with a defined distance $d_i$ and volume $V_i$, excretion level $Q_i$ is determined from the position of diffusion front 29 of the body fluid by correlation between the position of diffusion front 29 and volume $V_i$ of body fluid absorbed by absorbent element 12.

The method preferably comprises a step of identifying a time $T_i$ corresponding to the moment when the value of electric parameter $X_i$ of the pair of electrodes $C_i$ exceeds the threshold value $X_{is}$.

The data of electric parameter $X_i$ and of time $T_i$ are collected and transmitted by means of any known method to the data control and operating system.

The step of determining excretion level $Q_i$ can be followed by a step of computing an excretion flow rate. The excretion flow rate can be a global flow rate and/or an instantaneous excretion flow rate. The excretion flow rates are computed from the determined excretion level $Q_i$ and from the corresponding time $T_i$.

The global excretion flow rate or the instantaneous excretion flow rate is computed from a duration $\Delta T_{ii'}$. Duration $\Delta T_{ii'}$ corresponds to the time necessary for the body fluid to migrate into absorbent element 12 from one pair of electrodes $C_i$ to another pair of electrodes $C_{i'}$ and to cover the distance separating pairs $C_i$ and $C_{i'}$.

Duration $\Delta T_{ii'}$ is computed from times $T_i$ and $T_{i'}$ according to the following equation (1):

$$\Delta T_{ii'} = T_{i'} - T_i \quad (1)$$

For example purposes, global excretion flow rate $D_g$ and instantaneous excretion flow rate $D_i$ can be computed by the following equations (2) and (3):

$$D_g = (Q_5 - Q_1)/(T_5 - T_1) \quad (2)$$

$$D_i = (Q_2 - Q_1)/(T_2 - T_1) \quad (3)$$

The method for determining the excretion level $Q_i$ (or the excretion flow rate) can advantageously be coupled with conductivity measurements of the absorbed body fluid. By applying an electric voltage on each pair of electrodes $C_i$, the conductivity of the body fluid can be measured. The conductivity value of the solution does however enable the sweat loss of a person during an intense physical activity to be monitored. The salt concentration lost by the person can thus be known and this loss be compensated by administration of a suitable quantity of energy solution.

Example 1

The device is produced with an absorbent element 12 formed by a strip of absorbent paper marketed by the Wattman company under the reference PS 903. The electrodes are made from copper. Measuring means 16 are formed by a 3V battery and a 1 MOhm resistor 31.

The method for determining the excretion Level $Q_i$ (or the excretion flow rate using the excretion level) is performed from measurement of voltages $U_i$ at the terminals of resistor 31 versus time.

As represented in FIGS. 5 to 10, switching is preferably performed successively from one position to another so as to regularly scan the five channels associated with the five pairs of electrodes $C_1$, $C_2$, $C_3$, $C_4$ and $C_5$. In other words, when the value of voltage $U_i$ reaches a certain threshold, the time $T_i$ corresponding to the moment the threshold is reached is recorded, and the switch is activated so that the measured value becomes the voltage $U_{i+1}$ associated with the pair $C_{i+1}$.

From an inlet opening 20, an aqueous solution of sodium chloride with a concentration of 50 mM is input in regular manner by means of a syringe pusher 33 with a global flow rate fixed at 10 μl/min. The NaCl solution enables a body fluid such as sweat to be modeled. As diffusion front 29 progresses, absorbent element 12 passes under each first electrode $E^1_i$, along the diffusion path from a dry state to state imbibed by the body fluid.

The results obtained have been set out in the following table:

| Position of the diffusion front | $C_1$ | $C_2$ | $C_3$ | $C_4$ | $C_5$ |
|---|---|---|---|---|---|
| Corresponding figure | 6 | 7 | 8 | 9 | 10 |
| Volume absorbed during detection (μl) | 7 | 11.8 | 16.2 | 21.2 | 26.2 |
| Time $T_i$(s) | 0 | 29 | 54 | 85 | 115 |
| Instantaneous flowrate $D_i$ (μl/mn) | — | 9.9 | 10.6 | 9.7 | 10 |

From the collected data, the global flowrate $D_g$ can be computed according to equation (2). $D_g$ is equal to $(Q_5 - Q_1)/(T_5 - T_1)$ i.e.: $(26.2 - 7)/[(115 - 0)/60]$ i.e. 10.34 μl/min. The value of threshold voltage $U_{is}$ is fixed at 0.7V.

Example 2

The device is identical to the first example as are the measuring conditions with the exception of the fact that eight channels associated with eight pairs of electrodes $C_1$, $C_2$, $C_3$, $C_4$, $C_5$, $C_6$, $C_7$ and $C_8$ are scanned instead of five.

Figure 11:
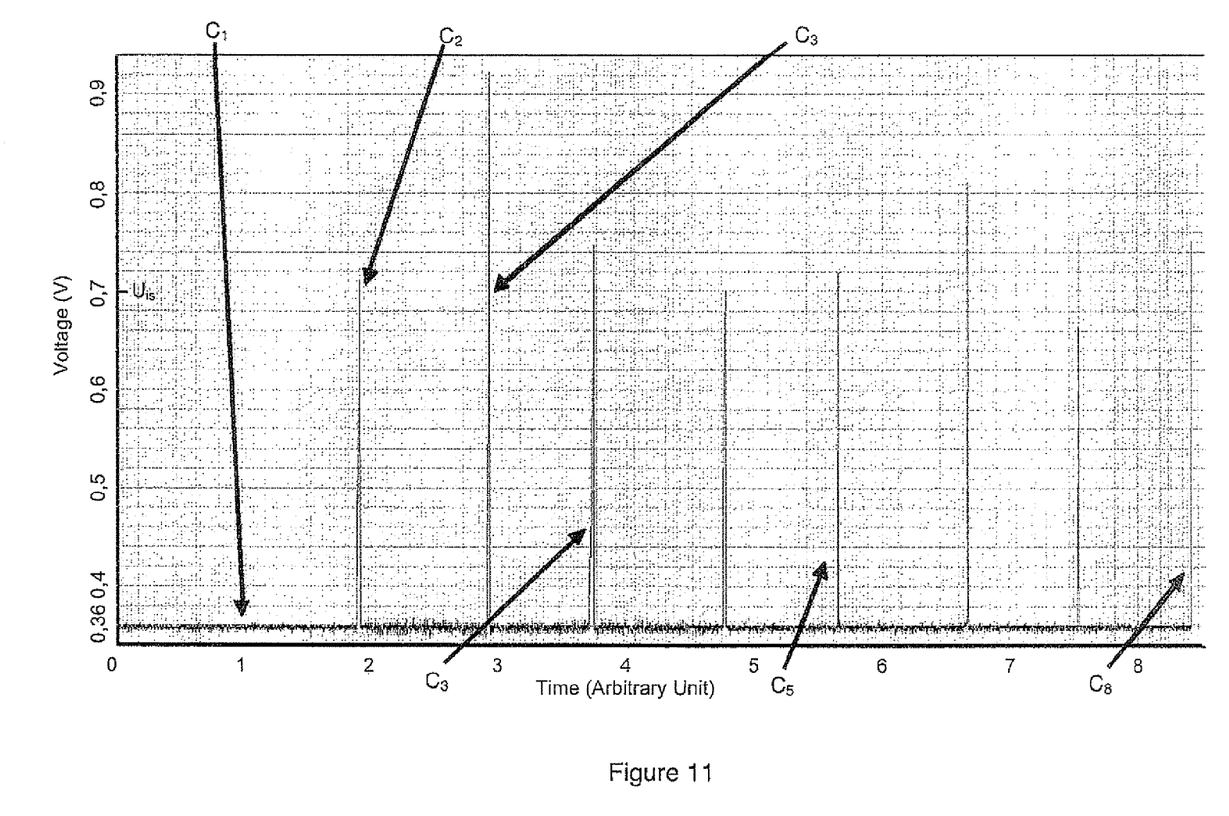
FIG. 11 is a graph representing the variation of the measured voltage (in V) versus time (in AU) taken from a device according to example 2.

The results obtained are represented in FIG. 11 and have been set out in the following table:

| | Position of the diffusion front | | | | | | | |
|---|---|---|---|---|---|---|---|---|
| | $C_1$ | $C_2$ | $C_3$ | $C_4$ | $C_5$ | $C_6$ | $C_7$ | $C_8$ |
| Volume absorbed during detection (μl) | 7 | 11.8 | 16.2 | 21.2 | 26.2 | 30.5 | 36.2 | 42 |
| Time $T_i$(s) | 0 | 29 | 54 | 85 | 115 | 139 | 174 | 210 |
| Instantaneous flowrate $D_i$ (μl/mn) | — | 9.9 | 10.6 | 9.7 | 10 | 10.7 | 9.8 | 9.7 |

From the collected data, the global flowrate $D_g$ can be computed according to equation (2). $D_g$ is equal to $(Q_8 - Q_1)/(T_8 - T_1)$ i.e.: $(42 - 7)/[(210 - 0)/60]$ i.e. 10 μl/min. The value of threshold voltage $U_{is}$ is fixed at 0.7V.

Figure 15:
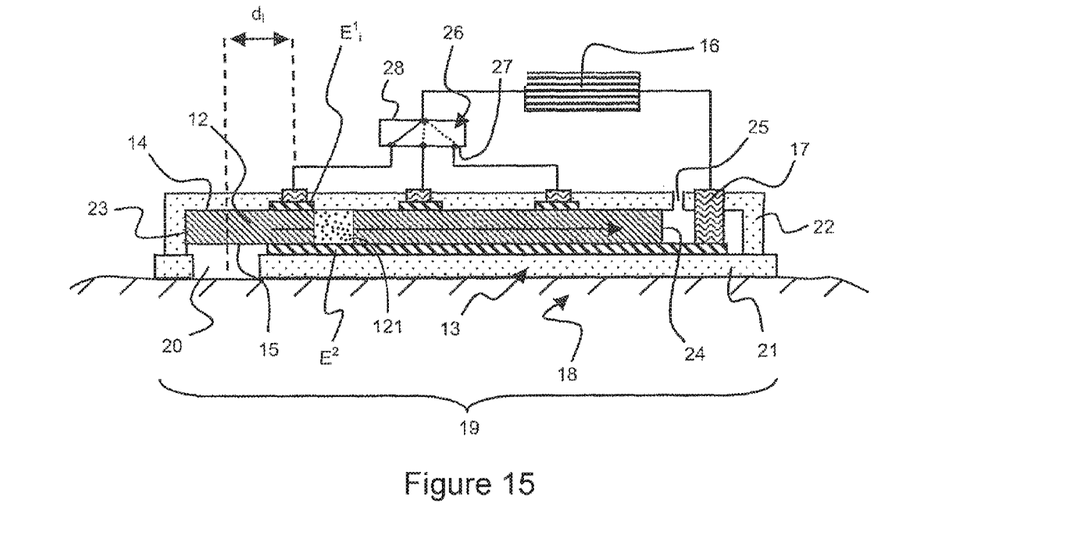
FIG. 15 schematically represents a device for determining an excretion flow rate of a body fluid according to a particular alternative embodiment of the invention.

According to an alternative embodiment shown in FIG. 15, absorbent element 12 comprises means/elements 121 for increasing the conductivity of the body fluid. The means for increasing the conductivity can be a conducting ink present in absorbent element 12 and situated between at least the electrodes of a pair of electrodes $C_i$. When the body fluid reaches the conducting ink, it dissolves or disperses thereby increasing the conductivity of absorbent element 12. The device comprising such an ink presents a higher sensitivity for measuring electric parameter $X_i$, and consequently enables excretion level $Q_i$ to be determined with greater precision.

Figure 16:
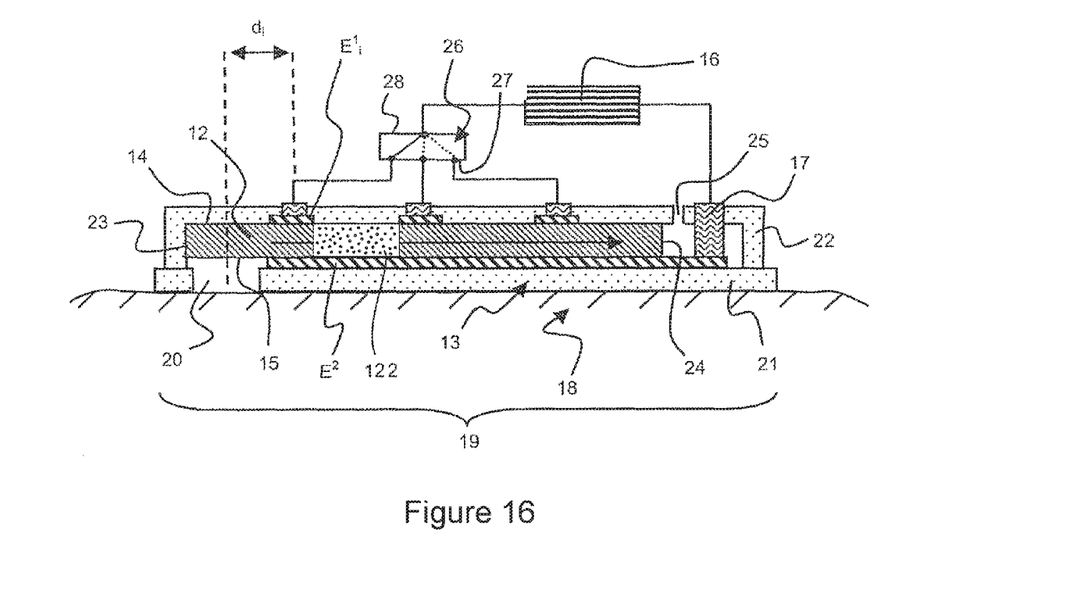
FIG. 16 schematically represents a device for determining an excretion flow rate of a body fluid according to another particular alternative embodiment of the invention.

According to another alternative embodiment shown in FIG. 16, absorbent element 12 comprises a colorimetric developer 122 of the presence of the first body fluid. According to a similar principle to the previous alternative embodiment, a colorimetric developer can advantageously be injected into absorbent element 12 between at least the electrodes of a pair of electrodes $C_i$, which developer changes color in contact with the body fluid. A non-conducting ink can for example be used in absorbent element 12. Easy and quick monitoring can thus advantageously complete the functions of the device.

Figure 12:
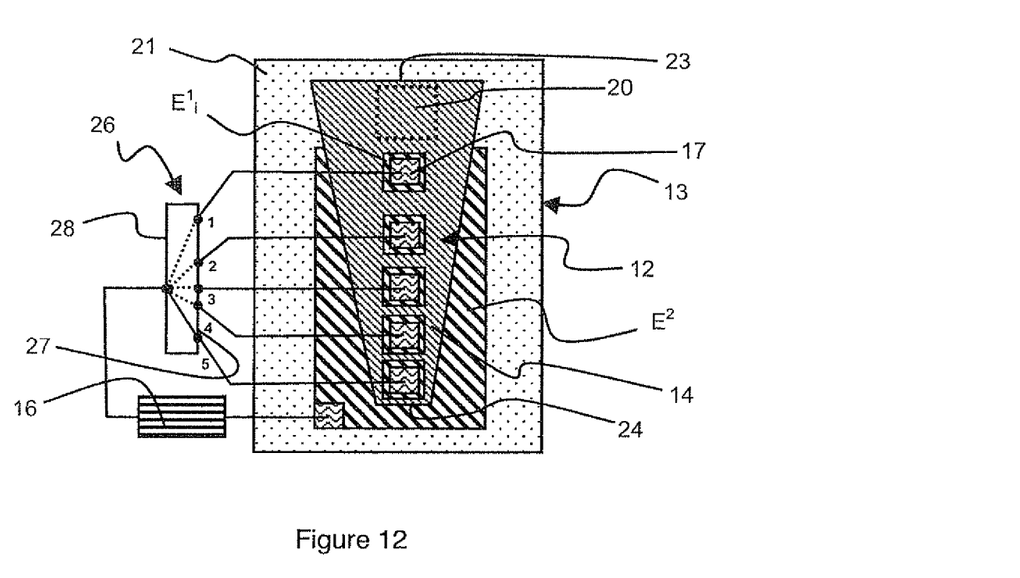
FIGS. 12 to 14 schematically represent three other particular embodiments of a device according to the invention, in top view.

According to a third embodiment represented in FIG. 12, the device is identical to the second embodiment with the exception of the fact that absorbent element 12 is in the form of a strip with a truncated cone-shaped cross-section having a large base and a small base. The inlet opening 20 is situated in proximity to the large base so that the absorbed body fluid converges towards the small base. The particular truncated cone shape of absorbent element 12 compensates the loss of migration speed observed along the migration path, moving away from inlet opening 20. The shape of the strip enables this drawback to be palliated, enhancing migration of the body fluid within absorbent element 12.

Figure 13:
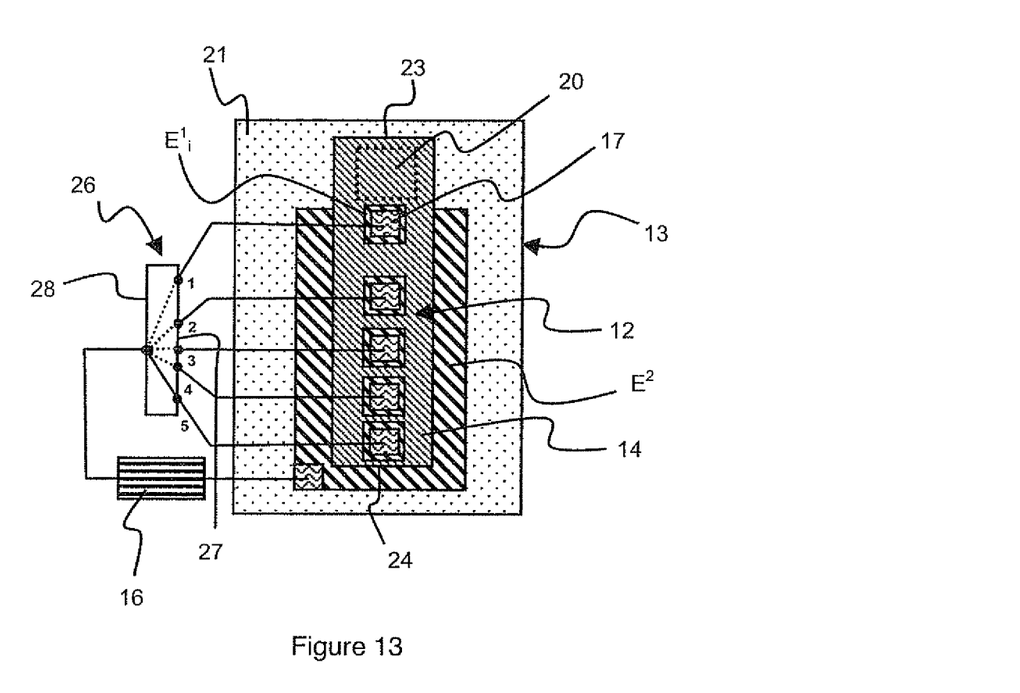

According to a fourth embodiment represented in FIG. 13, the device is identical to the second embodiment with the exception of the fact that the distance separating two adjacent first electrodes, respectively $E^1_i$ and $E^1_{(i+i)}$, reduces when moving away from inlet opening 20. As before, the object of this distinctive feature is to palliate the loss of migration speed of the body fluid along the migration path.

Figure 14:
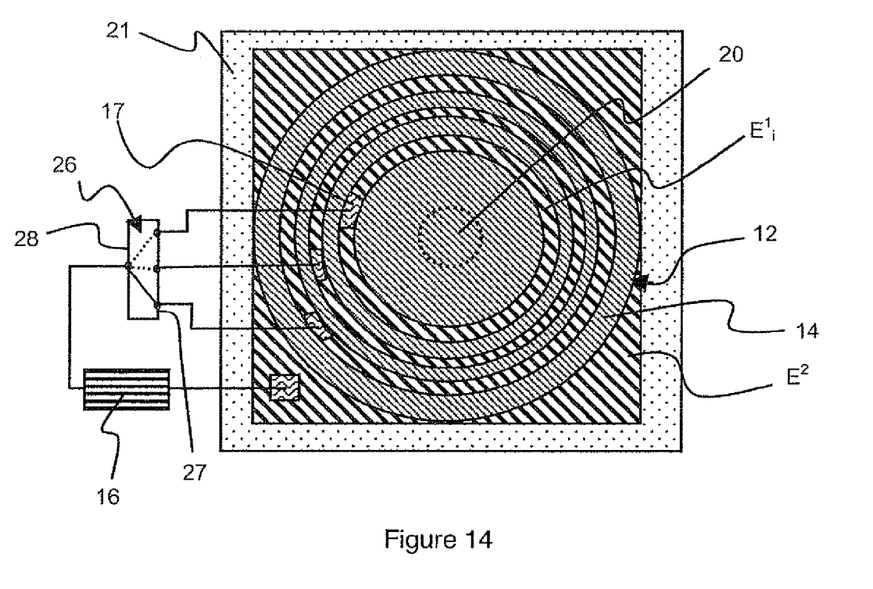

According to a fifth embodiment represented in FIG. 14, the device is identical to the second embodiment with the exception of the fact that the diffusion path of the body fluid is concentric starting from inlet opening 20. First electrodes $E^1_i$ are circular electrodes forming concentric circles on first main surface 14 of absorbent element 12, the centre of the circles being formed by inlet opening 20, and then moving successively away from inlet opening 20.

Although the examples described in the foregoing only concern devices for determining the excretion level $Q_i$ (or excretion flow rate) of a body fluid comprising a single second electrode $E_2$, the invention is however in no way limited to the embodiments which have been described for illustrative purposes only and which cannot limit the scope of the invention. It can thus be envisaged to produce an identical device to those described in the foregoing but comprising several second electrodes $E^2_i$. Second electrodes $E^2_i$ are then arranged in line according to an identical sequence to that of first electrodes $E^1_i$ and in parallel manner to said sequence. The person skilled in the trade is able to adapt the electric connection to enable coupling of the first and second electrodes, respectively $E^1_i$ and $E^2_i$, two by two to enable the diffusion front 29 of the body fluid to be followed by measurement of an electric parameter $X_i$ according to the same principle as the one described in the foregoing.

It can likewise be envisaged to produce a device that does not comprise a second electrode $E_2$. First electrodes $E^1_1$ are then coupled two by two with a suitable electric layout to form pairs of electrodes $C_i$. Excretion level $Q_i$ is determined according to an identical determination method to the one described in the foregoing.

The device according to the invention is particularly suitable for determining the perspiration flow rate of a person or of an animal. The device and also the method using such a device can advantageously be used to evaluate the hydric loss of the person or of the animal by perspiration, from determination of the excretion level $Q_i$ which corresponds in this case to a perspiration rate. What is meant by perspiration is the quantity of sweat excreted by secretion of the skin of a person or of an animal. The device can be used by sportsmen and sportswomen having intense physical activities requiring monitoring of the perspiration rate to check for possible dehydration of the sportsman or sportswoman. The device can likewise be integrated in protective clothing for workers, firemen or military.

Finally, the device can be integrated in diapers to enable the rate of filling of the diapers to be evaluated. The device therefore also finds an application in the field of monitoring of incontinence of elderly people or replacement of an infant or baby's diapers.

Unlike devices of the prior art, the device according to the invention enables the excretion level $Q_i$ of a body fluid by a person or an animal to be determined in reproducible, precise and dependable manner. The device according to the invention further presents the advantage of using a different pair of electrodes $C_i$ for each measurement, thereby avoiding imprecisions due to successive measurements on the same electrode. The method using such a device enables excretion of a body fluid of a person or an animal to be monitored in real time, by providing an excretion level $Q_i$ and a global or instantaneous flowrate of the body fluid. Furthermore, determination of the excretion level $Q_i$ according to the invention does not depend on the composition of the body fluid and is consequently not made erroneous by a variation of the concentration of the body fluid in the course of time, which is frequently observed in particular for sweat. Finally, the method according to the invention enables determination of the excretion level $Q_i$ and of the global or instantaneous flowrate to be coupled with conductivity measurements of the body fluid.

The invention claimed is:

1. A device for determining an excretion flow rate of a body fluid of a person or an animal wearing the device, the device comprising:
    an impermeable separating layer made of an impermeable material and designed to be placed in contact with a body of the person or the animal having a source of excretion of the body fluid, the impermeable separating layer defining a first opening configured for allowing inlet of the body fluid, an absorbent element configured to absorb the body fluid and to define a diffusion path from the first opening to an end of the absorbent element, the impermeable separating layer is disposed between the source of excretion of the body fluid and the absorbent element so as to separate the source of excretion of the body fluid and the absorbent layer and to cause absorption of the body fluid from the first opening to the end of the diffusion path,
    a set of at least three electrodes spaced apart from one another, two of said at least three electrodes are placed in sequential manner along the diffusion path,
    an impermeable film, the impermeable film forming an impermeable enclosure with the impermeable separating layer, the impermeable enclosure housing the absorbent element and the set of at least three electrodes, and a circuitry connected to the at least three electrodes and configured to:

define at least two pairs of electrodes by means of the at least three electrodes, and measure at least one electric parameter of a part of said absorbent element situated between said at least two pairs of electrodes so as to determine the excretion flow rate of the body fluid along the absorbent element, wherein the first opening in the separation layer is located before the electrodes in a fluid flow direction of the diffusion path and the separation layer has no other openings at or after the electrodes in the fluid flow direction of the diffusion path.

2. The device according to claim 1, wherein said set of electrodes is divided into at least two first electrodes placed on a first side of the absorbent element and one second electrode placed on a second side of the absorbent element, the second side being opposite of the first side and the second electrode facing the at least two first electrodes.

3. The device according to claim 2, wherein the set of electrodes comprises at least three first electrodes.

4. The device according to claim 1, wherein the set of electrodes is divided into at least two first electrodes placed on a first side of the absorbent element and at least two second electrodes placed on a second side of the absorbent element, the second side being opposite of the first side and each first electrode facing one of the second electrodes and wherein the circuitry is configured to define at least two pairs of electrodes, each pair of electrode comprising one of the first electrode and the facing second electrode.

5. The device according to claim 1, wherein the diffusion path of the body fluid is concentric starting from the first opening and wherein the two of said at least three electrodes are circular electrodes forming concentric circles on the absorbent element, the centre of the circles being formed by the first opening, and then moving successively away from said first opening.

6. The device according to claim 1, wherein the diffusion path of the body fluid is unidirectional and wherein the two of said at least three electrodes are arranged in line.

7. The device according to claim 6, wherein the absorbent element is in the form of a strip with a truncated cone-shaped cross-section having a large base and a small base so as to compensate loss of migration speed and wherein the first opening is situated in proximity to the large base so that the absorbed body fluid converges towards the small base.

8. The device according to claim 1, wherein the set of electrodes is divided into at least three first electrodes placed on a first side of the absorbing element, the distance separating two consecutive first electrodes decreasing when moving away from the first opening.

9. The device according to claim 1, wherein the absorbent element comprises elements for increasing conductivity of the body fluid.

10. The device according to claim 1, wherein said elements for increasing conductivity of the body fluid are conductive inks configured to be dissolved or dispersed by the body fluid.

11. The device according to claim 1, wherein the absorbent element comprises a colorimetric developer of the presence of the body fluid.

12. The device according to claim 1, comprising a selector switch configured to selectively form different pair of electrodes by means of the set of at least three electrodes so as to determine a position of a diffusion front of the body fluid in the absorbent element.

13. The device according to claim 1, wherein the circuitry is configured to monitor the flow rate of the body fluid in real time and continuously.

14. The device according to claim 1, wherein the at least three electrodes are disposed on surfaces of the absorbent element.

15. The device according to claim 1, wherein the at least three electrodes are disposed inside the absorbent element.

16. The device according to claim 1, wherein the body fluid is perspiration or urine.

17. A method for determining an excretion flow rate of a body fluid of a person or an animal, comprising the following steps:

providing a device worn by the person or animal comprising:

an impermeable separating layer made of an impermeable material and designed to be placed in contact with a source of excretion of the body fluid, the impermeable separating layer defining a first opening configured for allowing inlet of the body fluid, an absorbent element configured to absorb the body fluid and to define a diffusion path from the first opening to an end of the absorbent element, the impermeable separating layer is disposed between the source of excretion of the body fluid and the absorbent element so as to separate the source of excretion of the body fluid and the absorbent layer and to cause absorption of the body fluid from the first opening to the end of the diffusion path, a set of at least three electrodes spaced apart from one another, two of said at least three electrodes are placed in sequential manner along the diffusion path, an impermeable film, the impermeable film forming an impermeable enclosure with the impermeable separating layer, the impermeable enclosure housing the absorbent element and the set of at least three electrodes, and a circuitry connected to the at least three electrodes and configured to define at least two pairs of electrodes by means of the at least three electrodes and configured to measure at least one electric parameter of a part of said absorbent element situated between said at least two pairs of electrodes^ wherein the first opening in the separation layer is located before the electrodes in a fluid flow direction of the diffusion path and the separation layer has no other openings at or after the electrodes in the fluid flow direction of the diffusion path, bringing said device into contact with a body of the person or the animal having the source of excretion of the body fluid so as to position the first opening facing said source and to ensure flow of the excreted body fluid through the first opening to the absorbent element, measuring an electric parameter for each pair of electrodes, said measurement being successively performed from one pair of electrodes to the adjacent pair of electrodes in an order following the diffusion path, evaluating the position of a diffusion front of the body fluid on the diffusion path, relatively to the position of the electrodes, by comparing a value of the measured electric parameter with a predefined threshold value corresponding to flow of the body fluid between the electrodes of each pair of electrodes and, determining an excretion level from the position of the diffusion front by correlation between said position and a volume of body fluid absorbed by the absorbent element, identifying a time corresponding to a moment when the value of the electric parameter of each pair of electrodes reaches the threshold value, and determining a global excretion flow rate and/or an instantaneous excretion flow rate from said excretion level and from the corresponding time.

18. The method according to claim 17, wherein the global excretion flow rate or the instantaneous excretion flow rate is computed from a time period for the body fluid to migrate into the absorbent element from one pair of electrodes to another pair of electrodes and to cover the distance separating said pairs.

19. The method according to claim 17, wherein the measured electric parameter is selected from the group consisting of a conductivity, a voltage, a resistance, a capacitance and a global ion concentration.

20. The method according to claim 17, wherein the body fluid is perspiration or urine.

\* \* \* \* \*